United States Patent
Akdogan et al.

(10) Patent No.: US 10,160,588 B2
(45) Date of Patent: Dec. 25, 2018

(54) DISPENSING CARTRIDGE

(71) Applicant: Makefield LLC, Newtown, PA (US)

(72) Inventors: Kutadgu Akdogan, New York, NY (US); Christian Von Heifner, Brooklyn, NY (US); Dale Trigger, Brooklyn, NY (US); Kalyan C. Vepuri, Newtown, PA (US)

(73) Assignee: Hero Health, Inc., New York, NY (US)

( * ) Notice: Subject to any disclaimer, the term of this patent is extended or adjusted under 35 U.S.C. 154(b) by 254 days.

(21) Appl. No.: 15/174,187

(22) Filed: Jun. 6, 2016

(65) Prior Publication Data

US 2017/0001788 A1  Jan. 5, 2017

Related U.S. Application Data

(63) Continuation of application No. 14/214,828, filed on Mar. 15, 2014, now Pat. No. 9,358,500.
(Continued)

(51) Int. Cl.
*B65D 83/04* (2006.01)
*B01D 53/26* (2006.01)
(Continued)

(52) U.S. Cl.
CPC ......... *B65D 83/0409* (2013.01); *A61J 1/03* (2013.01); *A61J 7/0076* (2013.01); *A61J 7/02* (2013.01);
(Continued)

(58) Field of Classification Search
CPC ........ A61J 1/00; A61J 1/03; A61J 7/02; A61J 7/0076; A61J 7/0481; B65D 83/0409; B65D 81/268; B01D 53/261; G07F 11/44; G07F 11/00; G07F 17/0092; G07C 9/00134; H04N 7/188; G06F 19/3462; G06F 19/00

See application file for complete search history.

(56) References Cited

U.S. PATENT DOCUMENTS 3,224,634 A  12/1965 Semsch
4,402,425 A  9/1983 von Schuckmann et al.
(Continued)

FOREIGN PATENT DOCUMENTS

DE  102011112953  3/2013
EP  1360658  6/2008
(Continued)

OTHER PUBLICATIONS

USPTO, "U.S. Appl. No. 14/819,054 Notice of Allowance dated Jan. 18, 2018", 8 pages.
(Continued)

*Primary Examiner* — Patrick H Mackey
(74) *Attorney, Agent, or Firm* — Strategic Patents, P.C.

(57) ABSTRACT

A dispensing cartridge may be improved by the inclusion of an actuator and an agitator. Specifically, activation of the actuator may move the agitator within the cartridge to agitate the items and to direct one of the items into a position for dispensing. Concurrently, activation of the actuator may move a cap of the cartridge to align a dispensing hole with the position for dispensing, thereby allowing for the dispensing of a single item.

12 Claims, 7 Drawing Sheets

Related U.S. Application Data

(60) Provisional application No. 61/800,973, filed on Mar. 15, 2013.

(51) Int. Cl.

| | | |
|---|---|---|
| *A61J 7/02* | (2006.01) | |
| *G07F 11/44* | (2006.01) | |
| *A61J 1/03* | (2006.01) | |
| *A61J 7/00* | (2006.01) | |
| *G07C 9/00* | (2006.01) | |
| *H04N 7/18* | (2006.01) | |
| *A61J 7/04* | (2006.01) | |
| *G06F 19/00* | (2018.01) | |
| *G07F 9/02* | (2006.01) | |
| *G07F 11/00* | (2006.01) | |
| *G07F 17/00* | (2006.01) | |
| *B65D 81/26* | (2006.01) | |
| *B01D 53/04* | (2006.01) | |

(52) U.S. Cl.
CPC .......... *A61J 7/0481* (2013.01); *B01D 53/261* (2013.01); *B65D 81/268* (2013.01); *G06F 19/00* (2013.01); *G06F 19/3462* (2013.01); *G07C 9/00134* (2013.01); *G07F 9/026* (2013.01); *G07F 11/00* (2013.01); *G07F 11/44* (2013.01); *G07F 17/0092* (2013.01); *H04N 7/188* (2013.01); *B01D 53/0454* (2013.01)

(56) References Cited

U.S. PATENT DOCUMENTS

| | | | |
|---|---|---|---|
| 4,695,954 A | 9/1987 | Rose et al. | |
| 4,782,980 A | 11/1988 | Heimlich et al. | |
| 4,854,478 A | 8/1989 | Gyimothy | |
| 5,240,139 A | 8/1993 | Chirnomas | |
| 5,490,610 A | 2/1996 | Pearson et al. | |
| 5,502,944 A | 4/1996 | Kraft et al. | |
| 5,559,503 A | 9/1996 | Blahut | |
| 5,571,258 A | 11/1996 | Pearson | |
| 5,597,995 A | 1/1997 | Williams et al. | |
| 5,791,515 A | 8/1998 | Khan et al. | |
| 6,142,337 A | 11/2000 | Schreckenberg et al. | |
| 6,253,955 B1 | 7/2001 | Bower et al. | |
| 6,367,473 B1 | 4/2002 | Käfer et al. | |
| 6,371,297 B1 | 4/2002 | Cha | |
| 6,411,567 B1 | 6/2002 | Niemiec et al. | |
| 6,507,275 B2 | 1/2003 | Romano et al. | |
| 6,529,801 B1 | 3/2003 | Rosenblum | |
| 2,003,009 A1 | 5/2003 | De la Huerga | |
| 6,604,019 B2 | 8/2003 | Ahlin et al. | |
| 6,662,081 B1 | 12/2003 | Jacober et al. | |
| 6,685,678 B2 | 2/2004 | Evans et al. | |
| 6,732,884 B2 | 5/2004 | Topliffe et al. | |
| 6,892,941 B2 | 5/2005 | Rosenblum | |
| 6,948,634 B2 | 9/2005 | Evans et al. | |
| 7,006,894 B2 | 2/2006 | de la Huerga | |
| 7,073,685 B1 | 7/2006 | Giraud | |
| 7,155,306 B2 | 12/2006 | Haitin et al. | |
| 7,170,823 B2 | 1/2007 | Fabricius et al. | |
| 7,253,411 B2 | 8/2007 | Kaushal et al. | |
| 7,382,263 B2 | 6/2008 | Danowski et al. | |
| 7,395,214 B2 | 7/2008 | Shillingburg | |
| 7,404,500 B2 | 7/2008 | Marteau et al. | |
| 7,471,993 B2 | 12/2008 | Rosenblum | |
| 7,587,259 B2 | 9/2009 | Berg et al. | |
| 7,715,277 B2 | 5/2010 | de la Huerga | |
| 7,755,478 B2 | 7/2010 | Niemiec et al. | |
| 7,774,097 B2 | 8/2010 | Rosenblum | |
| 7,844,361 B2 | 11/2010 | Jean-Pierre | |
| 7,885,725 B2 | 2/2011 | Dunn et al. | |
| 7,944,342 B2 | 5/2011 | Sekura | |
| 7,978,564 B2 | 7/2011 | De La Huerga | |
| 7,996,106 B2 | 8/2011 | Ervin et al. | |
| 8,014,232 B2 | 9/2011 | Niemiec et al. | |
| 8,019,471 B2 | 9/2011 | Bogash et al. | |
| 8,116,907 B2 | 2/2012 | Hyde et al. | |
| 8,212,677 B2 | 7/2012 | Ferguson | |
| 8,326,455 B2 | 12/2012 | Dunn et al. | |
| 8,391,104 B2 | 3/2013 | de la Huerga | |
| 8,636,172 B2 | 1/2014 | Dunn et al. | |
| 8,666,539 B2 | 3/2014 | Ervin et al. | |
| 8,700,212 B1 | 4/2014 | Ives et al. | |
| 8,752,728 B2 * | 6/2014 | Tignanelli ................ A61J 1/03 221/15 |
| 8,887,603 B2 | 11/2014 | Mitani et al. | |
| 9,014,847 B2 | 4/2015 | Dunn et al. | |
| 9,235,689 B2 | 1/2016 | Ervin et al. | |
| 9,251,493 B2 | 2/2016 | Gershtein et al. | |
| 9,501,887 B2 | 11/2016 | Berg | |
| 2001/0002448 A1 | 5/2001 | Wilson et al. | |
| 2002/0032582 A1 | 3/2002 | Feeney, Jr. et al. | |
| 2002/0147526 A1 | 10/2002 | Siegel et al. | |
| 2004/0054436 A1 | 3/2004 | Haitin et al. | |
| 2004/0155780 A1 | 8/2004 | Rapchak et al. | |
| 2005/0098576 A1 | 5/2005 | Fenton et al. | |
| 2005/0230409 A1 | 10/2005 | von Schuckmann | |
| 2005/0240305 A1 | 10/2005 | Bogash et al. | |
| 2006/0058724 A1 | 3/2006 | Handfield et al. | |
| 2006/0213921 A1 | 9/2006 | Abdulhay et al. | |
| 2007/0007301 A1 | 1/2007 | Kaplan et al. | |
| 2007/0088461 A1 | 4/2007 | Haitin et al. | |
| 2007/0093932 A1 | 4/2007 | Abdulhay et al. | |
| 2007/0156282 A1 | 7/2007 | Dunn et al. | |
| 2008/0093371 A1 | 4/2008 | Ubidia et al. | |
| 2008/0114490 A1 | 5/2008 | Jean-Pierre et al. | |
| 2008/0300719 A1 | 12/2008 | Duke | |
| 2009/0069742 A1 | 3/2009 | Larsen | |
| 2009/0108016 A1 | 4/2009 | Brown et al. | |
| 2009/0134181 A1 | 5/2009 | Wachman et al. | |
| 2009/0167531 A1 | 7/2009 | Ferguson | |
| 2009/0182582 A1 | 7/2009 | Hammon | |
| 2009/0192648 A1 | 7/2009 | Namineni et al. | |
| 2009/0295575 A1 | 12/2009 | Kennedy et al. | |
| 2009/0299522 A1 | 12/2009 | Savir et al. | |
| 2010/0042255 A1 | 2/2010 | Boutin et al. | |
| 2010/0076595 A1 | 3/2010 | Nguyen | |
| 2010/0084420 A1 | 4/2010 | Van Den Broek et al. | |
| 2010/0096399 A1 | 4/2010 | Ratnakar et al. | |
| 2010/0193579 A1 | 8/2010 | Becker et al. | |
| 2010/0228567 A1 | 9/2010 | Wulf et al. | |
| 2010/0256808 A1 | 10/2010 | Hui et al. | |
| 2010/0270257 A1 | 10/2010 | Wachman et al. | |
| 2010/0305749 A1 | 12/2010 | Coe | |
| 2010/0318218 A1 | 12/2010 | Muncy, Jr. et al. | |
| 2011/0060448 A1 | 3/2011 | Gotou et al. | |
| 2011/0060457 A1 | 3/2011 | De Vrught et al. | |
| 2011/0160896 A1 | 6/2011 | Kim | |
| 2011/0166700 A1 | 7/2011 | Dunn et al. | |
| 2011/0251850 A1 | 10/2011 | Stephens | |
| 2012/0006708 A1 | 1/2012 | Mazur | |
| 2012/0041778 A1 | 2/2012 | Kraft et al. | |
| 2012/0044054 A1 | 2/2012 | Hussain et al. | |
| 2012/0101630 A1 | 4/2012 | Daya et al. | |
| 2012/0199650 A1 | 8/2012 | Horst et al. | |
| 2012/0316897 A1 | 12/2012 | Hanina et al. | |
| 2012/0323360 A1 | 12/2012 | Lavin | |
| 2012/0330460 A1 | 12/2012 | Henderson et al. | |
| 2013/0006652 A1 | 1/2013 | Vahlberg et al. | |
| 2013/0008918 A1 | 1/2013 | Cronin et al. | |
| 2013/0030566 A1 | 1/2013 | Shavelsky et al. | |
| 2013/0047986 A1 | 2/2013 | Goede et al. | |
| 2013/0110283 A1 | 5/2013 | Baarman et al. | |
| 2013/0134178 A1 | 5/2013 | Lu et al. | |
| 2014/0007806 A1 | 1/2014 | Stanton et al. | |
| 2014/0025199 A1 | 1/2014 | Berg et al. | |
| 2014/0236351 A1 | 8/2014 | Hyde et al. | |
| 2014/0263391 A1 | 9/2014 | Akdogan et al. | |
| 2014/0263423 A1 | 9/2014 | Akdogan et al. | |
| 2014/0263425 A1 | 9/2014 | Akdogan et al. | |
| 2014/0267719 A1 | 9/2014 | Akdogan et al. | |
| 2014/0277707 A1 | 9/2014 | Akdogan et al. | |
| 2014/0277710 A1 | 9/2014 | Akdogan et al. | |

(56) References Cited

U.S. PATENT DOCUMENTS

| | | |
|---|---|---|
| 2014/0278508 A1 | 9/2014 | Akdogan et al. |
| 2014/0278510 A1 | 9/2014 | McLean et al. |
| 2015/0090733 A1 | 4/2015 | Park |
| 2016/0039553 A1 | 2/2016 | Akdogan et al. |
| 2016/0039621 A1 | 2/2016 | Akdogan et al. |
| 2016/0042151 A1 | 2/2016 | Akdogan et al. |

FOREIGN PATENT DOCUMENTS

| | | |
|---|---|---|
| JP | 50132440 | 10/1975 |
| JP | 721583 | 4/1995 |
| JP | 2003252389 | 9/2003 |
| JP | 2005219785 | 8/2005 |
| WO | WO-2005115889 | 12/2005 |
| WO | WO-2009080309 | 7/2009 |
| WO | WO-2011054000 | 5/2011 |
| WO | WO-2014145218 | 9/2014 |
| WO | WO-2014145274 | 9/2014 |
| WO | WO-2016022714 | 2/2016 |

OTHER PUBLICATIONS

EPO, "EP Application Serial No. 15830466.7, Supplemental Search Report dated Dec. 11, 2017", 10 pages.

Japanese Patent Office, "JP Application Serial No. 2016-503306 Office Action dated Feb. 6, 2018", English and Japanese Translations, 11 pages.

USPTO, "U.S. Appl. No. 14/819,054, Non-Final Office Action dated Sep. 19, 2017", 8 pages.

USPTO, "U.S. Appl. No. 14/819,154, Notice of Allowance dated Apr. 7, 2017", 14 pages.

WIPO, "PCT Application No. PCT/US15/43848 International Preliminary Report on Patentability dated Feb. 16, 2017", 11 pages.

IP Australia, "AU Application Serial No. 2014233218, Examination Report dated May 26, 2017", 2 pages.

USPTO, "U.S. Appl. No. 14/214,797 Notice of Allowance dated Mar. 29, 2016", NPL-14, 11 pages.

USPTO, "U.S. Appl. No. 14/214,828 Notice of Allowance dated Mar. 29, 2016", 8 pages.

USPTO, "U.S. Appl. No. 14/819,125 Non-Final Office Action dated Oct. 5, 2016", 11 pages.

USPTO, "U.S. Appl. No. 14/214,737, Non-Final Office Action dated Feb. 10, 2016", 17 pages.

USPTO, "U.S. Appl. No. 14/214,779, Non-Final Office Action dated Dec. 18, 2015", 12 pages.

USPTO, "U.S. Appl. No. 14/214,797 Non-Final Office Action dated Feb. 24, 2016", 9 pages.

USPTO, "U.S. Appl. No. 14/214,828, Non-Final Office Action dated Dec. 4, 2015", 9 pages.

USPTO, "U.S. Appl. No. 14/819,154, Final Office Action dated Jul. 14, 2016", 11 pages.

USPTO, "U.S. Appl. No. 14/819,154, Non-Final Office Action dated Jan. 12, 2016", 12 pages.

EPO, "EP Application Serial No. 14765247.3, EP Search Report dated Aug. 23, 2016", 8 pages.

ISA, "International Application Serial No. PCT/US14/029940, Search Report and Written Opinion dated Oct. 28, 2014", 18 pages.

WIPO, "International Application Serial No. PCT/US14/30008, Preliminary Report on Patentability dated Sep. 24, 2015", 5 pages.

ISA, "International Application Serial No. PCT/US15/43848, Search Report and Written Opinion dated Dec. 28, 2015", 14 pages.

ISA, "International Application Serial No. PCT/US2014/030008, Search Report and Written Opinion dated Aug. 8, 2014", 7 pages.

* cited by examiner

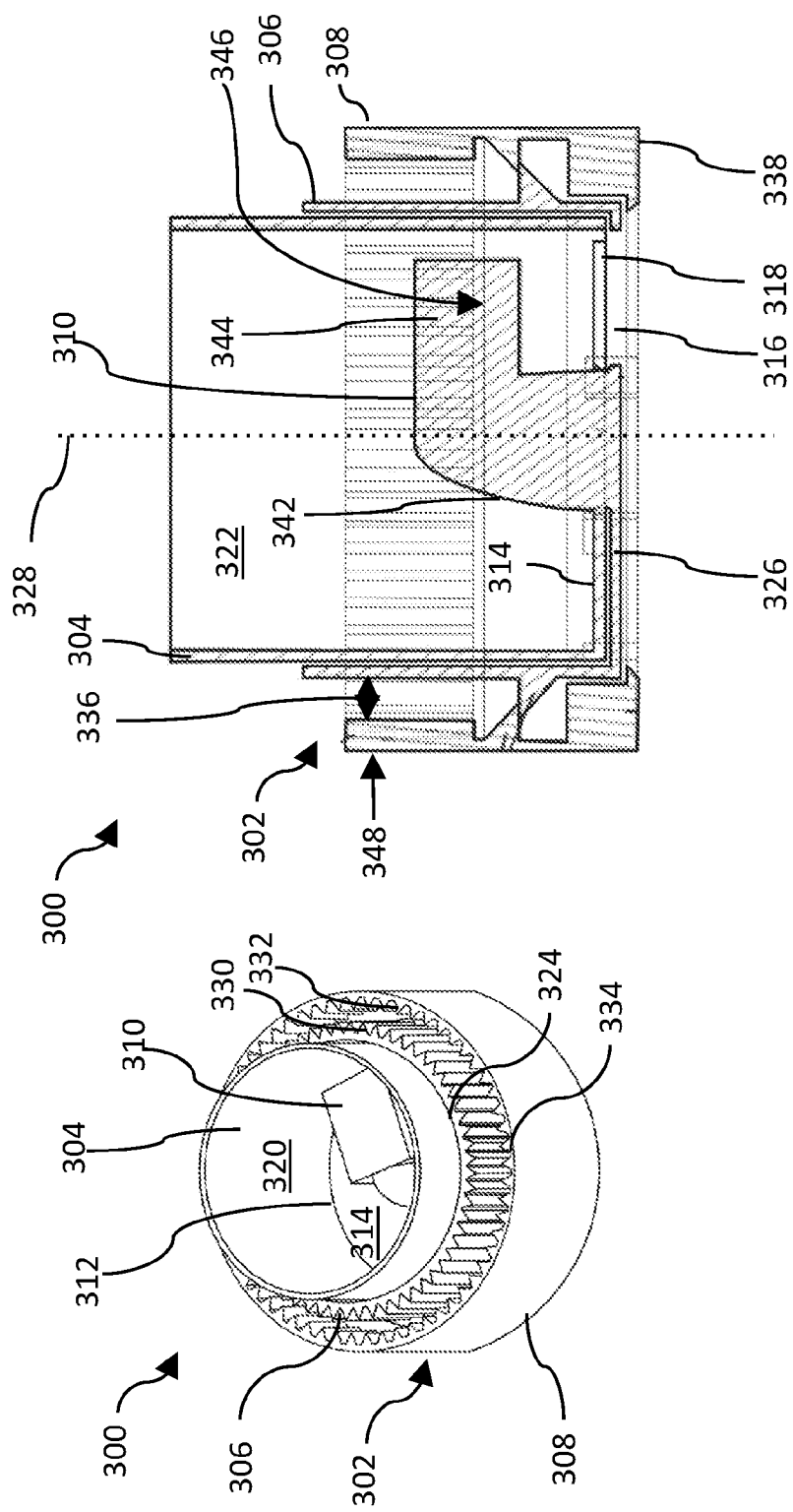

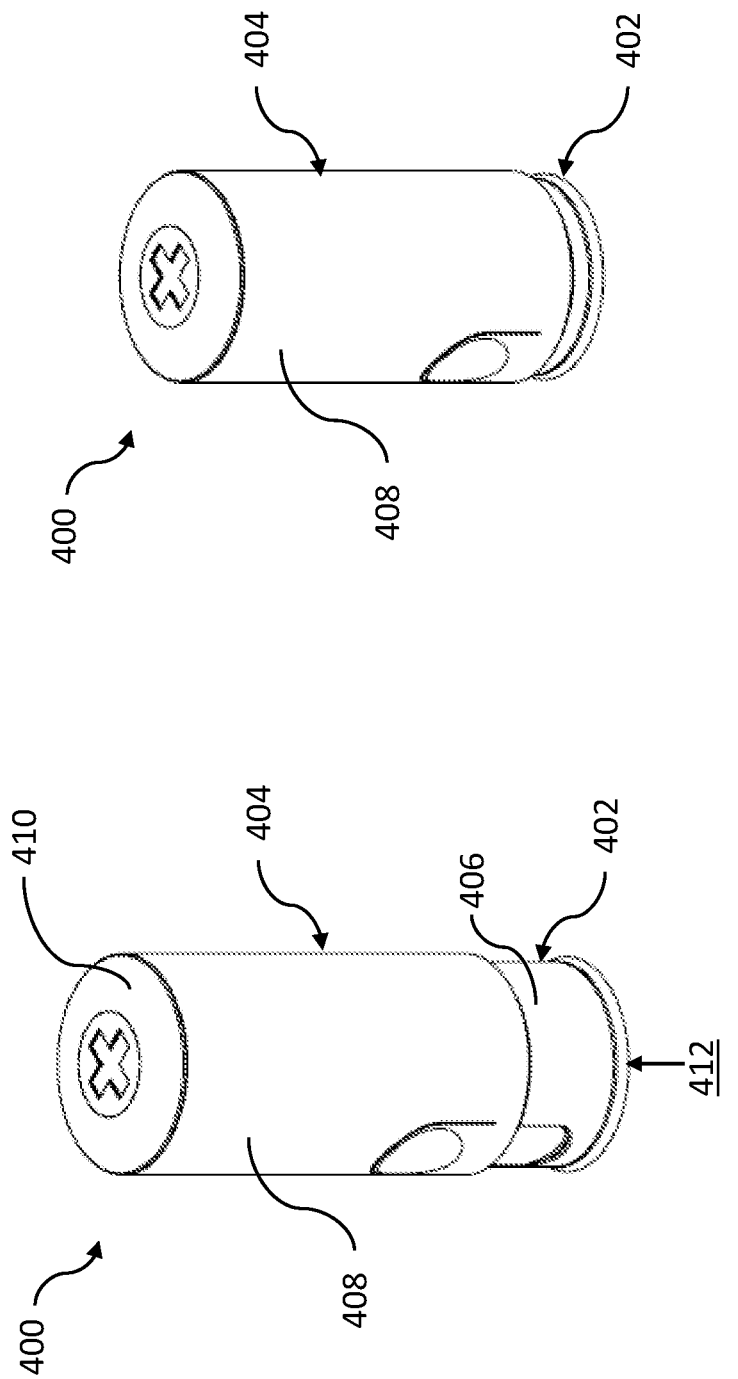

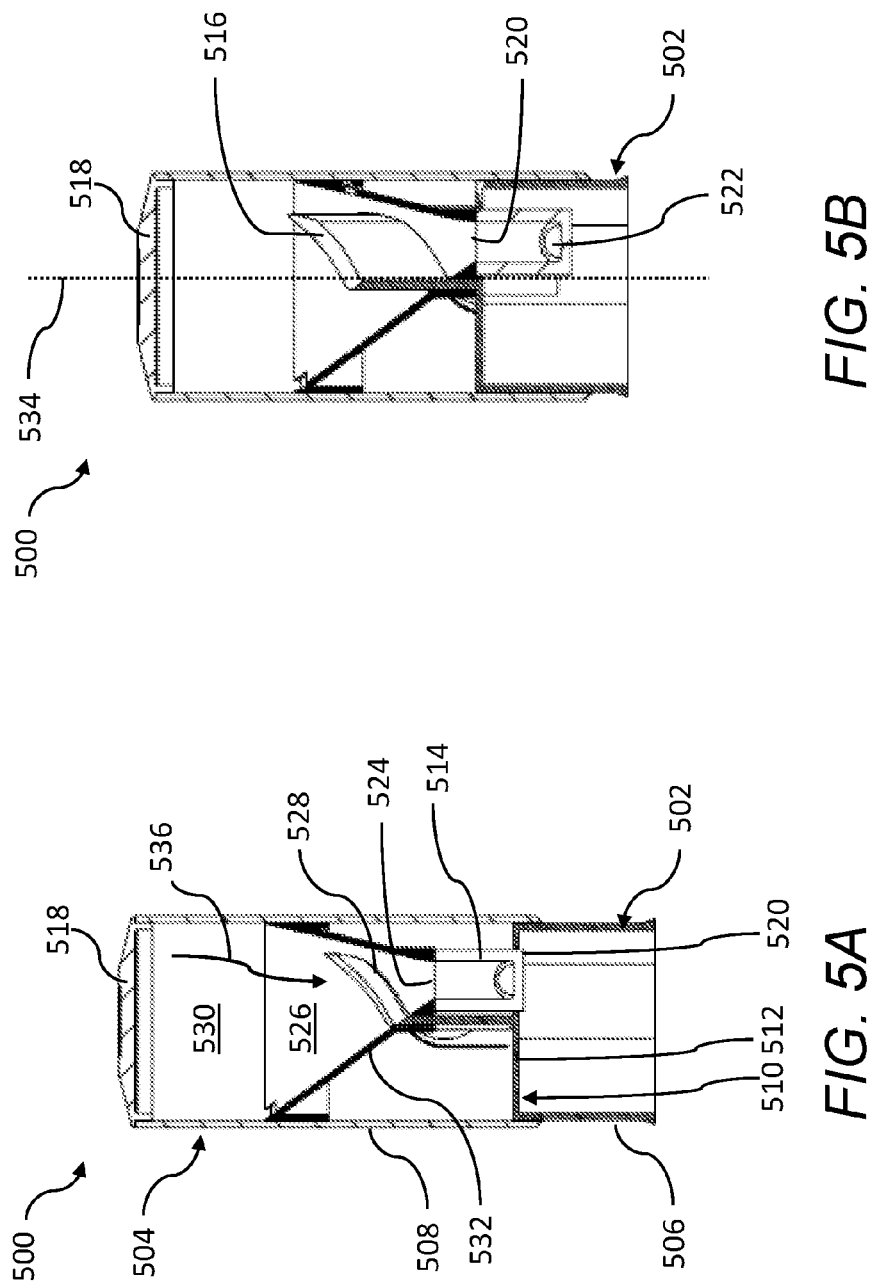

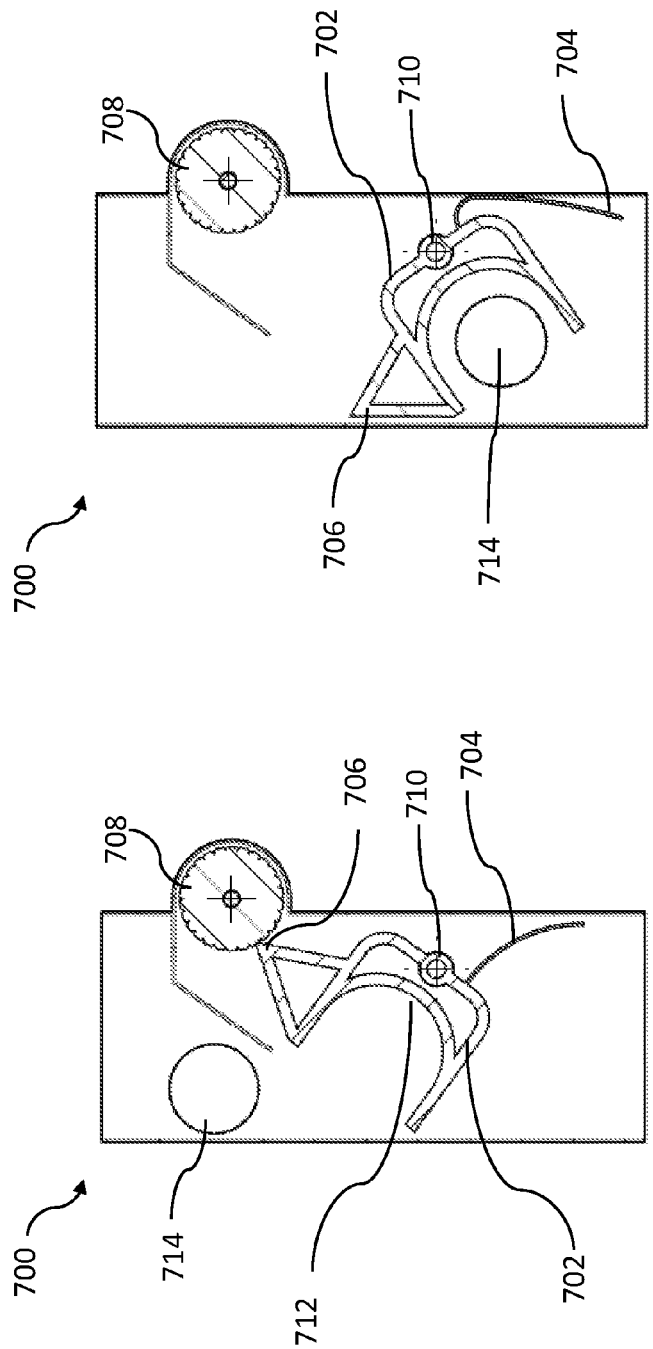

US 10,160,588 B2

DISPENSING CARTRIDGE

RELATED APPLICATIONS

This application is a continuation of U.S. patent application Ser. No. 14/214,828 filed on Mar. 15, 2014, which claims the benefit under 35 U.S.C. § 119(e) of U.S. Provisional Application No. 61/800,973 filed on Mar. 15, 2013, the entire content of each of the foregoing applications is hereby incorporated by reference.

FIELD OF THE INVENTION

This document generally relates to a dispensing cartridge, and more specifically to devices, systems, and methods for dispensing an item from a dispensing cartridge using an asymmetrical chute and agitator.

BACKGROUND

In general, cartridges to dispense single items (dispensables) may exist for many purposes, for example, for containers of consumables (e.g., pill bottles), and may include many functional and practical advantages. By way of example, pill bottles that dispense a single pill may allow a user to obtain a correct dosage, ease a user's ability to open the bottle and obtain a pill, assist in monitoring a patients' use of prescription drugs and supplements, and so forth. Although various mechanical devices attempt to isolate a single item during a dispensing process, these devices often include complex mechanisms that are unreliable, have problems with jams, cannot be adapted for a variety of items, or are difficult to use.

There remains a need for an improved dispensing cartridge.

SUMMARY

A dispensing cartridge may be improved by the inclusion of an actuator and an agitator. Specifically, activation of the actuator may move the agitator within the cartridge to agitate the items and to direct one of the items into a position for dispensing. Concurrently, activation of the actuator may move a cap of the cartridge to align a dispensing hole with the position for dispensing, thereby allowing for the dispensing of a single item.

In one aspect, a device includes a reservoir configured to hold items, and a chute coupled to the reservoir, where the chute includes a chute path to direct at least one of the items into a position for dispensing. The device may also include a housing about the reservoir and the chute, and a cap for the housing, where the cap includes a dispensing hole and is movably coupled relative to the chute to permit the dispensing hole to move into and out of alignment with the position for dispensing. The agitator may be positionable within the reservoir. The device may further include an actuator mechanically coupled to the agitator and the cap, where the actuator is configured to concurrently move the agitator within the reservoir to agitate the items and move the cap relative to the chute to align the dispensing hole with the position for dispensing.

In another aspect, a device includes a housing with a reservoir configured to hold items, a cap for the housing that includes a dispensing hole, and a chute coupled to the reservoir, where the chute includes a dispensing path to direct at least one of the items through the dispensing hole. The device may further include a rocker mechanism along the dispensing path in communication with the dispensing hole, where the rocker mechanism is pivotable relative to the chute and includes an item seat. The device may also include a biasing member mechanically coupled to the rocker mechanism, where the biasing member includes a biasing force that holds the rocker mechanism in a first position, and where the rocker mechanism is pivotable into a second position when a force is applied to the item seat causing compression of the biasing member. Also, the device may include a pin attached to the rocker mechanism, where the pin is movable with the rocker mechanism, and a dial counter disposed within the housing and rotatable relative to the housing, where the dial counter is configured to be engaged by the pin when the pin completes a pivoting motion (completing a pivoting motion includes a dispensing of an item). When the item for dispensing is directed onto the item seat of the rocker mechanism, a weight of the item for dispensing may concurrently compress the biasing member and may pivot the rocker mechanism into the second position where the item for dispensing is released from the item seat. Releasing the item for dispensing from the item seat may cause the biasing member to pivot the rocker mechanism back into the first position. The pin engaging the dial counter may cause the dial counter to rotate thereby counting a number of items dispensed by the device.

BRIEF DESCRIPTION OF THE DRAWINGS

The foregoing and other objects, features, and advantages of the devices, systems, and methods described herein will be apparent from the following description of particular embodiments thereof, as illustrated in the accompanying figures. The figures are not necessarily to scale, emphasis instead being placed upon illustrating the principles of the devices, systems, and methods described herein.

FIG. 3A is top perspective view of a rotational dispensing mechanism.

FIG. 3B is a cross-sectional view of a rotational dispensing mechanism.

FIG. 4A is an isometric view of a palm-press dispensing mechanism in an uncompressed state.

FIG. 4B is an isometric view of a palm-press dispensing mechanism in a compressed state.

FIG. 5A is a cross-sectional view of a palm-press dispensing mechanism in an uncompressed state.

FIG. 5B is a cross-sectional view of a palm-press dispensing mechanism in a compressed state.

FIG. 7A is a cross-sectional view of a counting mechanism in a first position.

FIG. 7B is a cross-sectional view of a counting mechanism in a second position.

DETAILED DESCRIPTION

Figure 1:
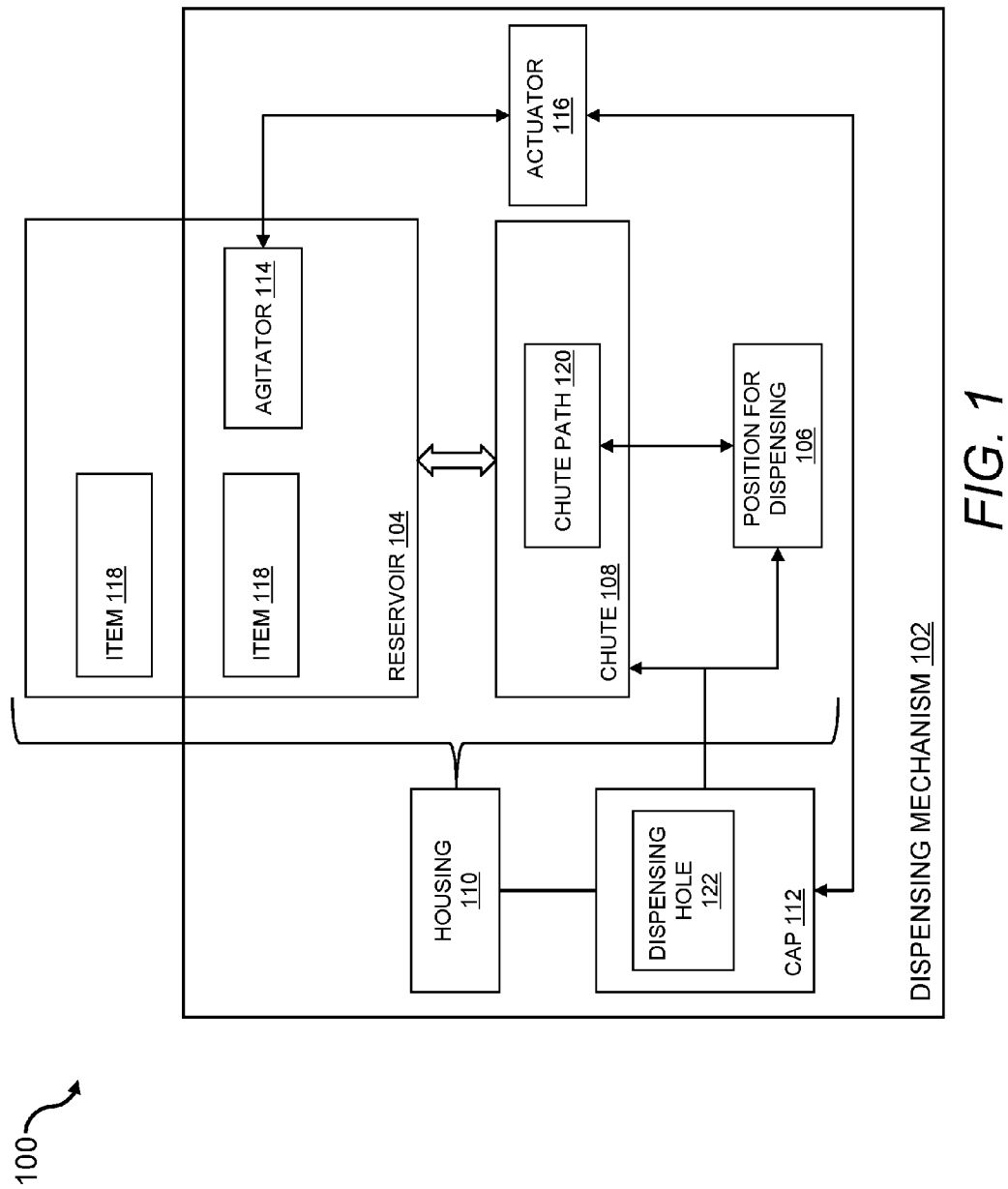
FIG. 1 shows a block diagram of a dispensing system.

The embodiments will now be described more fully hereinafter with reference to the accompanying figures, in which preferred embodiments are shown. The foregoing may, however, be embodied in many different forms and should not be construed as limited to the illustrated embodiments set forth herein. Rather, these illustrated embodiments are provided so that this disclosure will convey the scope to those skilled in the art.

All documents mentioned herein are hereby incorporated by reference in their entirety. References to items in the singular should be understood to include items in the plural, and vice versa, unless explicitly stated otherwise or clear from the text. Grammatical conjunctions are intended to express any and all disjunctive and conjunctive combinations of conjoined clauses, sentences, words, and the like, unless otherwise stated or clear from the context. Thus, the term "or" should generally be understood to mean "and/or" and so forth.

Recitation of ranges of values herein are not intended to be limiting, referring instead individually to any and all values falling within the range, unless otherwise indicated herein, and each separate value within such a range is incorporated into the specification as if it were individually recited herein. The words "about," "approximately," or the like, when accompanying a numerical value, are to be construed as indicating a deviation as would be appreciated by one of ordinary skill in the art to operate satisfactorily for an intended purpose. Ranges of values and/or numeric values are provided herein as examples only, and do not constitute a limitation on the scope of the described embodiments. The use of any and all examples, or exemplary language ("e.g.," "such as," or the like) provided herein, is intended merely to better illuminate the embodiments and does not pose a limitation on the scope of the embodiments. No language in the specification should be construed as indicating any unclaimed element as essential to the practice of the embodiments.

In the following description, it is understood that terms such as "first," "second," "top," "bottom," "up," "down," and the like, are words of convenience and are not to be construed as limiting terms.

Described herein are devices, systems, and methods for dispensing a single item from a dispensing cartridge. It will be understood that, "single item dispensing cartridge," "single-unit dispensing mechanism," and the like (i.e., any of the devices, cartridges, etc., described herein) may be used to dispense at least one item/unit at a time, which may include the dispensing of more than one item/unit. Stated otherwise, although embodiments described herein are primarily directed to dispensing a single item from a dispensing cartridge, in an aspect, the embodiments may be configured to dispense more than one single item. For example, in an aspect, a dispensing cartridge is configured to dispense a correct dose of medication, which may include more than one pill.

In general, the "item(s)," "unit(s)," "dispensable(s)," and related terms such as "dispensable unit" are intended to refer broadly to an item, combination of items, composition, component, material, compound or the like that can be dispensed in unit or continuous form.

While a "dispensable" or "item" may be any unit that can be dispensed, the term "consumable" or "consumable unit" is intended to refer to dispensables that are intended to be consumed by a user. Consumables are intended to include a wide array of ingestible consumable items and form factors for same. For example, consumable units may include one or more of pills, capsules, tablets, chewables, lozenges, dissolvables, sprinkles, dissolve-in-mouth micro-capsules, orally disintegrating tablets, chewable tablets (including jelly beans, gummies, and the like), gums, and so forth, as well as continuous form consumables such as liquids or powders, solutions, pastes, and suspensions, and combinations thereof. The consumables may also or instead include items provided as free powders, powder sachets, liquids, liquid sachets, vials, cups, cases, other storage forms, and so forth. More generally, the consumable units may be any composition for consumption in bulk, individual, individual pre-packaged, group pre-packaged and/or mixed item package form. For bulk form compositions, the "consumable unit" may be a predetermined portion for dispensing such as a teaspoon of liquid, a number of pills, a milligram of powder or the like, or a similar predetermined portion for dispensing or mixing into a compound locally created for dispensing prior to or after dispensing.

Similarly, the content of each consumable unit may vary significantly and may include but are not limited to prescription medication, non-prescription or over-the-counter medication, nutritional supplements, vitamin supplements, mineral supplements, veterinary medications, veterinary nutritional supplements, and so forth. Consumable units may also or instead include food and other items such as sugar, seeds, candies, snacks, pet treats, or other foods and the like, as well as any other pharmaceuticals, neutraceuticals, or other consumable items not identified above. These consumables that are intended to be ingestible are also referred to herein as "ingestibles" or "ingestible units."

While consumables may include items for consumption in the convention sense of ingestion as described above, consumables may also or instead include disposable items or the like that are intended for one time use. Thus, as used herein a "disposable" may be any consumable intended for a use other than ingestion. This may, for example, include disposable medical items such as dressings, bandages, Band-Aids, gauze, syringes, thermometers, individually packaged units of antibacterials and the like, as well as other items such as hearing aids, contact lenses and so forth that can be dispensed in individual units for one time use. This may also or instead include continuous form items not intended for ingestion including personal care items such as toothpaste, toothpicks, soap, sanitizer, moisturizer, cotton swabs and the like, as well as other household items such as glue, batteries, latex gloves, and so forth. All such disposables may be a form of consumable as those terms are used herein, and consumables may similarly be a form of dispensable.

It will be understood that while the foregoing terms (item, dispensable, consumable, ingestible, disposable) may be variously used in this disclosure to describe embodiments of the invention, the inventive concept generally applies to any and all such items/dispensables, and any description of one type of dispensable will be understood to refer to all such dispensables except where specifically noted to the contrary. Thus, for example, a container for consumable items will be understood to similarly teach a container for dispensable items, a container for ingestible items, and a container for disposable items.

In general, the "dispensing mechanisms" described herein may include dispensing cartridges, containers, packages, bottles, and the like, that are capable of dispensing one or more items. The dispensing mechanisms may be single-unit dispensing mechanisms, including, without limitation: (1) a spring-slider dispensing mechanism where a user may pull a trigger or the like and a unit falls out, which may include a durable cavity and agitating wedge technique to prevent jamming and mis-dosing; (2) a palm-press dispensing mechanism where a user may press the cartridge into their palm (e.g., with their other hand) and a unit is dispensed into the palm, which may include a durable agitator and asymmetrical chute to prevent jamming and mis-dosing; (3) a rotational dispensing mechanism where a user may twist the exterior cylinder and the units align within, where approximately every 120 degrees one unit falls out, where the unit alignment prevents jamming and mis-dosing; (4) a blister-doser dispensing mechanism where a user may push a blister strip forward, which severs material to dispense single blister unit; and (5) a thumb-press dispensing mechanism where a user may depress the top of the cartridge with their thumb and one unit is presented at the bottom of the cartridge. Three of these mechanisms are explained in more detail below, along with a dispensing system that may include a dispensing mechanism with features shared throughout each of these embodiments. A counting mechanism that may be adapted for use with any of the dispensing mechanisms described herein, or other dispensing mechanisms, is also explained in more detail below.

FIG. 1 shows a block diagram of a dispensing system 100, which includes a dispensing mechanism 102. The dispensing mechanism 102 may include a reservoir 104, a position for dispensing 106, a chute 108, a housing 110, a cap 112, an agitator 114, and an actuator 116. The dispensing mechanism 102 may be used to dispense a single item or multiple items. The dispensing mechanism 102 may be may be fully disposable, partially disposable, or fully reusable.

The reservoir 104 may be configured to hold a plurality of items 118, which may be any of the types of items described herein. The reservoir 104 may be included wholly within the dispensing mechanism 102, partially within the dispensing mechanism 102, or completely separate from the dispensing mechanism 102. For example, the reservoir 102 may be housed within a separate container that is attachable to the dispensing mechanism. The attachment may be accomplished using a snap-fit connection, a screw connection, a friction-fit connection, a pronged connection, a permanent magnet connection, an electromagnet connection, and the like, or any combination thereof. The attachment may be achieved through a feature on the housing 110. The connection may be permanent or temporary, where the container may be removed and replaced from the dispensing mechanism 102 and the dispensing mechanism 102 may be reusable. The reservoir 104 may be any type of container known in the art for housing items (e.g., temporarily or permanently). Similarly, the dispensing mechanism 102 may be configured to engage with more than one other container having a reservoir 104 or any number of reservoirs, having the same or different items. Such a configuration may be useful for many purposes, including, without limitation, item mixing. The reservoir 104 and/or housing 110 may be an environmentally sealed container. The reservoir 104 may be a cartridge (e.g., a single-dose or single-unit dispensing container, a multi-dose, or multi-unit dispensing container), a bottle (e.g., pill bottle, medicine bottle, and the like), and so forth. For example, the reservoir 104 may offer similar protection characteristics to existing pill bottles (e.g., against moisture, and the like). The reservoir 104 may include any of the following, without limitation: (1) use of plastic materials; (2) tamperproof aluminum foil seal on the reservoir 104; (3) cotton wool inside the reservoir 104 to prevent transportation damage to the contents; (4) desiccant for moisture management, which may be in a small bag/package in the reservoir 104 or in a separate desiccant chamber; and so on. The reservoir 104 may also include a bag or the like, for example, a re-sealable bag.

The position for dispensing 106 may generally be any position within the dispensing mechanism 102 where an item is present before being dispensed. "Dispensing" or the like, as used throughout this document, shall include the release of an item from the dispensing mechanism 102. The release may include release to a user, e.g., into the palm of a user's hand, or the release into another structure. For example, in one aspect, an attachment is coupled to the housing 110 by an attachment mechanism, where the item is dispensed through the dispensing hole 122 and into the attachment. The position for dispensing 106 may be in communication with the chute path 120, as indicated by the arrows in FIG. 1.

The chute 108 may generally include any structure to direct an item into the position for dispensing 106, which may include a structure that forms a chute path 120. The chute path 120 may be formed by any of the following, alone or in combination: the chute 108, the housing 110, the cap 112, the agitator 114, the actuator 116, the reservoir 104, the position for dispensing 106, and so on. The chute 108 may be symmetrical or asymmetrical in shape as well as with respect to an axis of the dispensing mechanism 102, reservoir 104, housing 110, or other component. For example, the chute 108 may include asymmetrically arranged surfaces about an axis of the reservoir 104. The asymmetrically arranged surfaces may form the chute path 120. In one aspect, there is more than one chute 108, for example, positioned to receive the items from corresponding containers and guide the items to a user-accessible location. The reservoir 104 may connect to the chute 108 using a snap retaining feature or the like. For example, the reservoir 104 may connect to the chute 108 via clips, friction fit, sliders, and the like.

The housing 110 may generally house the items and/or the components of the dispensing mechanism 102. For example, the housing 110 may include the reservoir 104, chute 108, and the position for dispensing 106. In one aspect, the housing 110 also includes the cap 122, the agitator 114, and the actuator 116. The housing 110 may be made from any material used for dispensing devices, including, without limitation, plastics, metals, woods, and so on.

The cap 112 may generally be a top/bottom for the housing 110, e.g., to seal (permanently or temporarily) the housing 110. The cap 112 may be part of the housing 110 or a separate component that may be connected to the housing 110 via a snap-fit connection, screw connection, a friction-fit connection, magnetic connection, and so on. The cap 112 may include a dispensing hole 122. The dispensing hole 122 may be any void, orifice, exit path, and the like, that may release an item during a dispensing operation. The item may be released by gravity or forced through the dispensing hole 122, e.g., through a mechanical or chemical means. In one aspect, item may be released by a combination of gravity fed and powered dispensing. The cap 112 may be movably coupled relative to the chute 108 to permit the dispensing hole 122 to move into and out of alignment with the position for dispensing 106. In this manner, the cap 112 may cooperate with at least one of the actuator 116, the agitator 114, the chute 108, the housing 110, and the position for dispensing 106.

The agitator 114 may be positionable within the reservoir 104 (or chute 108 or other area) to agitate the items 118. The agitation of the items 118 may assist in directing the items 118, for example, directing one of the items into the position for dispensing 106 and directing another one of the items away from the position for dispensing 106. The agitator 114 may be symmetrical or asymmetrical in shape as well as with respect to an axis of the dispensing mechanism 102, reservoir 104, housing 110, or other component. The agitator 114 may be in communication and engagement with the actuator 116, cap 112, housing 110, chute 108, chute path 120, reservoir 104, or other component. The agitator 114 may be an asymmetrical vertical agitator or asymmetrical horizontal agitator.

The actuator 116 may be mechanically coupled to at least one of the agitator 114 and the cap 112. The actuator 116 may be configured to concurrently move the agitator 114 within the reservoir 104 to agitate the items 118, and to move the cap 112 relative to the chute 108 to align the dispensing hole 122 with the position for dispensing 106. The actuator 116 may be actuated, e.g., by a person or by mechanical device.

A spring-slider dispensing mechanism will now be discussed.

Figure 2B:
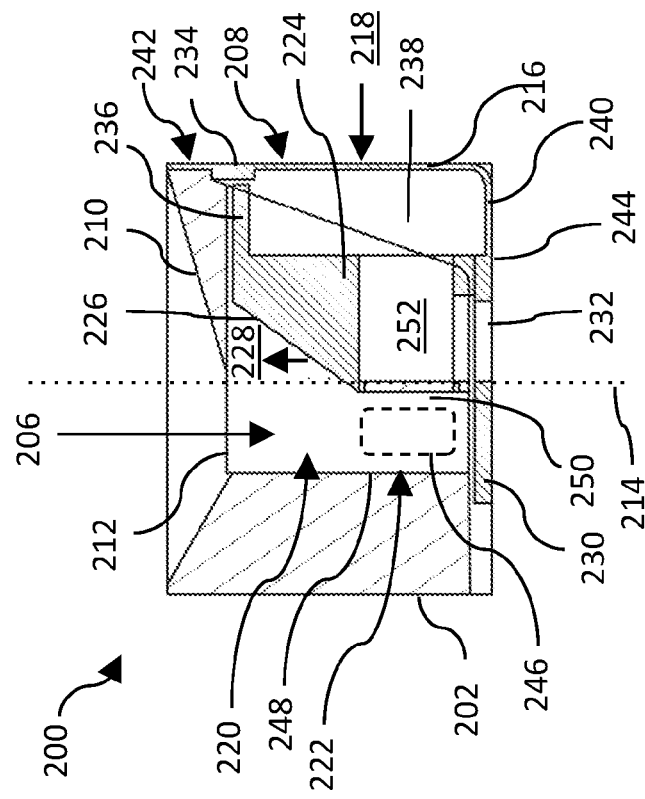
FIG. 2B is a cross-sectional view of a spring-slider dispensing mechanism.
Figure 2A:
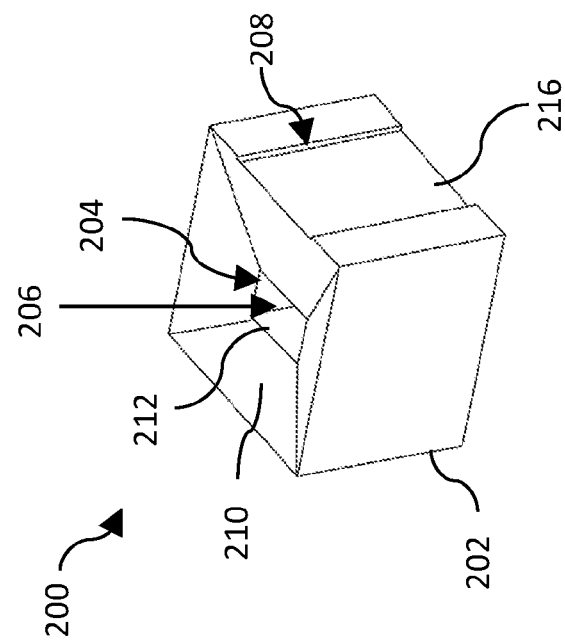
FIG. 2A is an isometric view of a spring-slider dispensing mechanism.

FIGS. 2A and 2B show an implementation of a dispensing mechanism. In one aspect, the dispensing mechanism is a spring-slider dispensing mechanism 200 that includes a housing 202, a chute 204, a chute path 206, and an actuator 208. In general, the spring-slider dispensing mechanism 200 may function such that when a user pushes/presses the actuator 208 (e.g., with their finger), the components of the spring-slider dispensing mechanism 200 create an agitation of the items included therein, which facilitates at least one item to exit the spring-slider dispensing mechanism 200, thereby completing a dispensing action (e.g., dispensing a single item).

The housing 202 may generally house the items within the spring-slider dispensing mechanism 200 and the components of the spring-slider dispensing mechanism 200. The housing 202 may include a reservoir configured to hold any category of items as described herein, including, without limitation, unit-form or continuous-form consumables. Additionally, or alternatively, the housing 202 may be configured to engage with a container including a reservoir. The housing 202 may be generally formed by other components of the spring-slider dispensing mechanism 200. For example, as shown in FIG. 2B, the exterior of the spring-slider dispensing mechanism 200 may include the arm 216 and the cap 230.

The chute 204 may generally include any structure to direct the item into a position for dispensing, which may include a structure that forms a chute path 206 as described herein. As shown in FIG. 2A, the chute 204 may include ramped surfaces 210 leading to a chute hole 212, where the ramped surfaces 210 direct items into the chute hole 212, e.g., using the force of gravity to urge the items into the chute hole 212. The ramped surfaces 210 may be asymmetrically arranged such that the chute 204 is an asymmetrical chute. For example, the ramped surfaces 210 may include individual surfaces with different slopes, or the chute hole 212 may be arranged such that it is offset from a central axis 214 of the spring-slider dispensing mechanism 200 (as shown in FIG. 2B). Alternatively, in one aspect, a symmetrical chute 204 may be provided. As shown in FIG. 2A, the chute 204 may include four ramped surfaces 210, but a skilled artisan will understand that a greater number of ramped surfaces 210 may be provided, or a smaller number of ramped surfaces 210 may be provided. Additionally, many configurations for the chute 204 may be possible. For example, the chute 204 may include a substantially funnel-shaped structure.

The chute path 206 may be a path that leads to a position for dispensing, for example, the chute path 206 may be a path that leads from a reservoir to the position for dispensing. The chute path 206 may be formed by the chute 204, or generally by the housing 202, or by other components/ structures within the spring-slider dispensing mechanism 200. The chute 206 may direct an item into the position for dispensing. As shown in FIG. 2A, the chute path 206 may include the path leading to the chute hole 212, which may include a path along the ramped surfaces 210. The chute path 206 may also or instead include the path through the chute hole 212, and continuing down the spring-slider dispensing mechanism 200 to a position for dispensing. The chute path 206 may be asymmetrical in an implementation. Alternatively, the chute path 206 may be symmetrical in an implementation. As shown in FIG. 2B, the chute path 206 may lead down from the chute 204 into the chamber 220 and eventually to the position for dispensing 222. The chute path 206 may also be influenced by the ramp 226 included on the agitator 224, as well as the agitator 224 itself because of its proximity to, and its communication with, the chamber 220 and the position for dispensing 222. The shape of the chute path 206 may be useful in configuring the units therein, e.g., items in the housing 202 may be aligned with their longest side vertical, due to the tight fit of the chute path 206, as shown by the item 246 in FIG. 2B.

The actuator 208 may include an arm 216. The arm 216 may be acted upon by a force generally in the direction of the arrow 218, which may then cause an agitation of the items included in the housing 202, which may also facilitate an item to exit the spring-slider dispensing mechanism 200. The force may be a pushing force that moves the arm 216 from a first position (as shown in the figures) to a second position in which the arm 216 moves in the direction of the arrow 218, which may include a deformation (e.g., an elastic deformation) of the arm 216. After the pushing force is released, the arm 216 may automatically return to the first position where it retains its original shape. The returning of the arm 216 to the first position may be accomplished through an elastic property of the arm 216 and/or through a biasing means such as a spring or the like.

In general, the actuator 208 may act as a "button" or the like to initiate the dispensing of an item. As shown in FIG. 2B, the actuator 208 may be mechanically coupled to the agitator 224. For example, the actuator 208 may include an arm 216, where the arm 216 is engaged to the agitator 224 through an agitator engagement portion 234 that cooperates with an arm engagement portion 236 of the agitator 224. The agitator engagement portion 234 may include a protrusion on the arm 216, and the arm engagement portion 236 may include an elongated member connected to the agitator 224. The arm 216 may be disposed adjacent to an arm deformation area 238, which is a void that accommodates at least a portion of the arm 216 when the arm 216 is actuated by a user.

FIG. 2B shows a cross-sectional view of an implementation of a spring-slider dispensing mechanism 200. FIG. 2B clearly shows the chamber 220, the position for dispensing 222, the agitator 224 with the ramp 226, a second arrow 228 showing a sliding motion of the agitator 224 from a first position to a second position, and a cap 230 with a dispensing hole 232.

The arm 216 may be made from the same material as the housing or a different material. In one aspect, the arm 216 is a deformable plastic or the like. The arm 216 may also or instead include a leaf spring or the like. The arm 216 may also or instead include a slidable button or the like, which may be non-deformable. As shown in FIG. 2B, the arm 216 may include a substantially L-shaped structure, with at least one flexible portion 240. The arm 216 may be attached to the spring-slider dispensing mechanism 200 through the use of a hinge 242 or the like, which may be disposed in the vicinity of the agitator engagement portion 234. The arm 216 may also or instead be attached by a glue, friction fit, joint, pin, screw, or the like. Alternatively, the arm 216 may be cantilevered to the housing 202 (e.g., the arm 216 may be integral with the housing 202—e.g., molded with the housing 202 when made from a plastic or the like), where the cantilevered end may also be disposed in the vicinity of the agitator engagement portion 234. The arm 216 may also include a cap engagement portion 244, which engages with the cap 230 such that movement of the arm 216 facilitates movement of the cap 230. In one aspect, the arm 216 includes at least a portion of the cap 230 (e.g., the arm 216 and cap 230 may be one piece). The actuator 208 thus may actuate a dispensing in the spring-slider dispensing mechanism 200 by (1) moving/sliding the agitator 224, and (2) moving/sliding the cap 230 thereby aligning the position for dispensing 222 with the dispensing hole 232.

The first arrow 218 generally shows the direction of the pushing force that may be applied to the arm 216. One of ordinary skill will recognize that this is merely one example of the direction of force that may be applied to the arm 216. For example, the force may be applied from the corner of the L-shape of the arm 216 (i.e., diagonally).

The chamber 220 may be included in a base of the chute path 206. The chamber 220 may include the position for dispensing 222. As shown in FIG. 2B, the chamber 220 may be sized and shaped to align one of the items for dispensing, which may be an oblong-shaped item 246. The chamber 220 may be formed by an interior housing wall 248 and an agitator box wall 250. The position for dispensing 222 may generally be any position within the spring-slider dispensing mechanism 200 where an item is present before being dispensed.

The agitator 224 may include a positionable component within the housing 202 that is configured to agitate the items and to direct at least one of the items through the chute path 206 into the position for dispensing 222. The agitator 224 may include a ramp 226 adjacent to the chute path 206 on a top portion of the agitator 224. The agitator 224 may be configured to move in the direction shown by the second arrow 228 in FIG. 2B, where such movement may be a sliding motion. A skilled artisan will recognize that the agitator 224 may be configured to move in other directions. When the agitator 224 is moved by the actuator 208, the ramp 226 may be configured to move with the agitator 224 into the chute path 206 to urge items towards the reservoir in the direction of the second arrow 228 (up towards the chute hole 212) while one of the items 246 remains in the chamber 220 for dispensing through the dispensing hole 232. The agitator 224 thus may agitate the items in the spring-slider dispensing mechanism 200 by pushing items not to be dispensed away from the chamber 220, while trapping an item 246 in the chamber 220 to be dispensed. The agitator 224 may be disposed adjacent to (e.g., above) an agitator box 252. The agitator box 252 may be a void disposed adjacent to the agitator box wall 250.

The cap 230 may be disposed on, or be part of, the housing 202. The cap may include a dispensing hole 232. The cap 230 may be movable, where such movement provides for the dispensing of an item. For example, the cap 230 may include a structure that prevents the release of items included in a reservoir of the spring-slider dispensing mechanism 200 when the cap 230 in a first position (as shown in FIG. 2B), and the cap 230 may permit the release of an item through the dispensing hole 232 when the cap 230 is moved into a second position. The first position may include the dispensing hole 232 out of alignment with the position for dispensing 222, while the second position includes the dispensing hole 232 in alignment with the position for dispensing 222. As discussed above, the actuator 208 may be mechanically coupled to the cap 230, where the actuator 208 is configured to move the cap 230 relative to the chute 204 (or chute path 206) to align the dispensing hole 232 with the position for dispensing 222. The cap 230 may be replaceable and/or interchangeable, for example, to adapt to different sized/shaped items.

The operation of a spring-slider dispensing mechanism will now be described.

In operation, a user may actuate the actuator 208 by applying a pushing force to the arm 216 in the direction shown by the first arrow 218. The pushing force may be applied by the user's finger, e.g., using only one hand. The pushing of the arm 216 may concurrently cause the arm 216 to (1) move the agitator 224 within the reservoir relative to the chute 204 to agitate the items and to direct one of the items 246 into the position for dispensing 222, and (2) move the cap 230 relative to the chute 204 to align the dispensing hole 232 with the position for dispensing 222. Specifically, the agitator engagement portion 234 of the arm 216 may contact the arm engagement portion 236 of the agitator 224 such that when the arm 216 moves in the direction of the first arrow 218, the agitator 224 moves in the same direction, i.e., the agitator 224 slides from a first position to a second position when the arm 216 is actuated by the pushing force. The first position may include the dispensing hole 232 out of alignment with the position for dispensing 222 and the second position may include the dispensing hole 232 in alignment with the position for dispensing 222. The sliding of the agitator 224 from the first position to the second position may also move the ramp 226 into the chute path 206, which urges items (i.e., items not to be dispensed during this operation) in the direction of the second arrow 228 towards the reservoir (i.e., chute hole 212) while one of the items 246 remains in the chamber 220 for dispensing through the dispensing hole 232. Because of the concurrent movement of the cap 230, which moves the dispensing hole 232 in alignment with the position for dispensing 222, the item 246 may be free to drop from the chamber 220 through the dispensing hole 232, thereby being dispensed from the spring-slider dispensing mechanism 200.

The spring-slider dispensing mechanism 200 may include childproofing.

As used throughout this document, "childproofing" and the like shall be any feature that may hinder, prevent, obstruct, burden, deter, etc. the ability of a child to dispense an item. For example, childproofing may include compliance with one or more industry standards including, without limitation, ISO 8317, ISO 13127, ASTM D3475, and the like. Any reference to a force required to actuate the devices, systems, and methods described herein, when including a childproofing feature, may be a force large enough to create a childproof feature of the device, e.g., a force that complies with an industry standard. Similarly, any reference to a difficulty to actuate the devices, systems, and methods described herein, when including a childproofing feature, may be a difficulty in order to create a childproof feature of the device, e.g., a difficulty that complies with an industry standard.

The childproofing in the spring-slider dispensing mechanism 200 may be enabled by the pushing force to actuate the actuator 208. Specifically, the pushing force to actuate the arm 216 may be equal to a force large enough to create a childproof feature of the device. In addition, or in the alternative, the childproofing may be enabled by a latch on the housing 202 (not shown) or tabs (not shown) that are squeezed by the user for the arm 216 to freely move. Other childproofing features may also be present in the spring-slider dispensing mechanism 200.

A rotational dispensing mechanism will now be discussed.

FIGS. 3A and 3B show an implementation of a rotational dispensing mechanism 300 that includes a housing 302 with an inner layer 304, a middle layer 306, and an outer layer 308. The rotational dispensing mechanism 300 may further include an agitator 310. In general, the rotational dispensing mechanism 300 may function such that when a user rotates the middle layer 306, the agitator 310 concurrently aligns items around a circumference of the inner layer base 314 and directs one of the items toward a middle layer hole 316. Additionally, rotation of the middle layer 306 may align the middle layer hole 316 with an inner layer hole 318 thereby allowing release of one of the items.

The housing 302 may include the inner layer 304, middle layer 306, and outer layer 308 all together, individually, or any combination thereof.

The inner layer 304 may include the inner layer base 314 and inner layer walls 320, which together form a reservoir 322. The reservoir may also or instead be included in a container to be attached to the rotational dispensing mechanism 300. For example, the inner layer 304 may be connected via a screw thread to a container having a reservoir that includes the items (not shown, but would be located vertically above the mechanism shown in FIGS. 3A and 3B). This connection may also be through other means, including, without limitation, a snap-fit, a friction fit, and so on. The inner layer 304 may include at least one inner layer hole 318 disposed about a circumference of the inner layer base 314. As explained below, the inner layer holes 318 may align with the middle layer hole 316 a number of times per revolution of the middle layer 306 (e.g., 1, 2, 3, etc. times per full revolution, depending on the number of inner layer holes 318), which may allow for the items to exit the rotational dispensing mechanism 300. For example, an item may be dispensed once for every 120 degrees that the middle layer 306 is rotated, or another amount of rotation. In order to aid alignment of the items along the circumference of the inner layer base 314, the inner layer base 314 may include inner layer pins (not shown), which may be projections extending up from the inner layer base 314. The inner layer pins may align a single item with each inner layer hole 318, and may prevent other items from following the aligned item as it is dispensed from the rotational dispensing mechanism 300. The inner layer 304 may be made from the same material as the remainder of the housing 302, or it may be made from a different material.

The middle layer 306 may be disposed around the inner layer 304 and rotatably coupled to the inner layer 304 such that the middle layer 306 is able to rotate relative to the inner layer 304. The middle layer 306 may include middle layer walls 324 that at least partially surround the inner layer walls 320. The middle layer 306 may include a middle layer base 326, which includes at least one middle layer hole 316. The middle layer hole 316 may be disposed on the middle layer base 326 offset from the central axis 328 of the reservoir 322. The middle layer hole 316 may be the dispensing hole for the rotational dispensing mechanism 300. The middle layer base 326 may at least partially surround the inner layer base 314. The middle layer 316 may include the agitator 310 protruding from the middle layer base 326, where the agitator 310 protrudes through the inner layer base 326 and into the reservoir 322. The middle layer 306 may optionally include a means for engagement with an outer layer 308 such that rotation of the outer layer 308 by a user also rotates the middle layer 306 about the inner layer 304. For example, the middle layer walls 320 may include a first set of gear teeth 330 that cooperate with a second set of gear teeth 332 on the outer layer walls 334 such that engagement of the gear teeth 330, 332 allows the middle layer 306 and the outer layer 308 to rotate together relative to the inner layer 304. The middle layer walls 320 and the outer layer walls 334 may be separated by a first distance 336, where a user must squeeze the outer layer walls 334 to engage the first set of gear teeth 330 with the second set of gear teeth 332. The middle layer 306 may be connected to a container having a reservoir that includes the items, in addition to or instead of the inner layer 304 connecting to the container. The middle layer 306 may be made from the same material as the remainder of the housing 302, or it may be made from a different material.

The outer layer 308 may be disposed around the middle layer 306 and coupled to the middle layer 306 in a manner that permits the outer layer 308 to engage and rotate the middle layer 306. The outer layer 308 may include outer layer walls 334 that at least partially surround the middle layer walls 324, where the walls 324, 334 may be separated by the first distance 336. The outer layer 308 may include an outer layer base 338, which may envelope at least a portion of the middle layer base 326. The outer layer 308 may be connected to the middle layer 306 through protruding rings or the like, which are disposed on the middle layer 306 and outer layer 308. The protruding rings may allow the middle layer 306 to snap irreversibly onto the outer layer 308 during manufacture. Other means for connection are also or instead possible, as will be evident to a skilled artisan. The outer layer 308 may be connected to a container having a reservoir that includes the items, in addition to or instead of the inner layer 304 or middle layer 306 connecting to the container. The outer layer 308 may be made from the same material as the remainder of the housing 302, or it may be made from a different material.

In one aspect, the outer layer 308 is only present in an embodiment with a childproofing feature. Stated differently, in one aspect, the rotational dispensing mechanism 300 may only include the inner layer 304 and the middle layer 306.

The agitator 310 may agitate the items and direct at least one of the items into the position for dispensing, i.e., onto an inner layer hole 318 (e.g., between the inner layer pins). The agitator 310 may include a substantially parabolic protrusion located at or near the central axis 328 that extends from the middle layer 306. The agitator 310 may rotate within the reservoir 322 when the middle layer 306 is rotated. The agitator 310 may include a rear wall 342 that is sloped such that it directs items onto the inner layer base 314. The agitator 310 may include an agitator arm 344 that extends in a direction substantially normal to the central axis 328. The agitator arm 344 may extend above the middle layer hole 316 and may include at least one face 346 having a substantially V-shaped surface that is configured to align items around the circumference of the inner layer base 314. Specifically, the agitator arm 344 may be configured to direct one of the items toward the middle layer hole 316 and to direct another one of the items away from the middle layer hole 316 when the agitator 310 rotates. Stated differently, when the middle layer 306 is rotated, the agitator 310 rotates, which in turn moves the agitator arm 344 circumferentially around the reservoir 322, which agitates the items. The agitation may also include arranging the items around the circumference of the bottom of the inner layer 304, e.g., due to the agitator 310 protruding into the reservoir 322 along the central axis 328. The agitation may also or instead include directing an item towards the inner layer hole 318 (and possibly the aligned middle layer hole 316) while forcing other items away through the movement of the agitator arm 344 and the shape of the face 346.

The chute in the rotational dispensing mechanism 300 may be formed by the inner layer walls 320. The chute path may be formed by any combination of the inner layer walls 320 and the agitator 310 (e.g., the rear wall 342, agitator arm 344, or face 344 of the agitator 310), or any of these components individually. The cap may be formed by the base of the housing 302, which may be formed by any combination of inner layer base 314, the middle layer base 326, and the outer layer base 338, or any of these components individually. Alternatively, the cap may be formed by a separate structural piece. The actuator of rotational dispensing mechanism 300 may be any one of the inner layer 304, the middle layer 306, or the outer layer 308, or any combination thereof. For example, the actuator may be the outer layer 308 in an implementation where the outer layer 308 is engaged with the middle layer 306 to rotate the middle layer 306. Alternatively, the actuator may be formed by a separate structural piece.

The operation of a rotational dispensing mechanism will now be described.

In operation, a user may actuate the rotational dispensing mechanism 300 by rotating the middle layer 306 about the inner layer 304. The rotation of the middle layer 306 may concurrently rotate the agitator 310 and the middle layer base 326. Rotation of the agitator may align items around the circumference of the inner layer base 314, where the agitator arm 344 directs one of the items toward an inner layer hole 318 or the middle layer hole 316 and directs another one of the items away from an inner layer hole 318 or the middle layer hole 316. Rotation of the middle layer base 326 may align the middle layer hole 316 with one of the inner layer 318 holes thereby allowing release of one of the items through the holes 316, 318.

The rotational dispensing mechanism 300 may include childproofing.

The childproofing in the rotational dispensing mechanism 300 may be enabled by the inclusion of the outer layer 308. Specifically, the outer layer 308 may be configured such that it can only engage the middle layer walls 324 when a squeezing force is applied to the outer layer 308. In this manner, the middle layer 306 may only rotate when the outer layer 308 is rotated and the squeezing force is applied. This squeezing force, shown by the force direction arrow 348, may be a force large enough to create a childproof feature of the rotational dispensing mechanism 300. In this manner, if a user does not squeeze the outer layer walls 334 with a minimum required squeezing force, the gear teeth 330, 332 will not engage. In addition, or in the alternative, an implementation may include an actuating arm (not shown) that allows engagement of the middle layer 306 (e.g., the first set of gear teeth 330) without squeezing the outer layer walls 334, because the actuating arm may directly engage the middle layer 306 (e.g., the first set of gear teeth 330).

A palm-press dispensing mechanism will now be discussed.

FIGS. 4A and 4B show an implementation of a palm-press dispensing mechanism 400. Specifically, FIG. 4A shows the outside of a palm-press dispensing mechanism 400 in an uncompressed state, and FIG. 4B shows the outside of a palm-press dispensing mechanism 400 in a compressed state. In general, the palm-press dispensing mechanism 400 may function such that when a user presses the palm-press dispensing mechanism 400 (e.g., against their palm), the components of the palm-press dispensing mechanism 400 create an agitation of the items included therein, which facilitates at least one item to drop down and exit the palm-press dispensing mechanism 400, thereby completing a dispensing action (e.g., dispensing a single item). As shown in FIGS. 4A and 4B, the palm-press dispensing mechanism 400 may generally include a housing having a first sleeve 402 and a second sleeve 404.

The first sleeve 402 may include first sleeve walls 406 and a base that includes a cap (not shown in FIGS. 4A and 4B).

The second sleeve 404 of the housing may include second sleeve walls 408 and a top 410. The second sleeve 404 may slidably engage with the first sleeve 402 such that, when a pressing force normal to the cap is applied to an end of the device (e.g., in a direction shown by arrow 412), the first sleeve 402 and the second sleeve 404 slide relative to one another along the first and second sleeve walls 406, 408 thereby creating a compressed state for the palm-press dispensing mechanism 400 (as shown in FIG. 4B) where the base and the top 410 are separated by a smaller distance than the distance between the base and the top 410 when the palm-press dispensing mechanism 400 is in an uncompressed state (as in FIG. 4A).

FIGS. 5A and 5B also show an implementation of a palm-press dispensing mechanism 500. Specifically, FIG. 5A shows a cross-sectional view of a palm-press dispensing mechanism 500 in an uncompressed state, and FIG. 5B shows a cross-sectional view of a palm-press dispensing mechanism 500 in a compressed state. In general, and as discussed above, the palm-press dispensing mechanism 500 may include a housing having a first sleeve 502 and a second sleeve 504, where the first sleeve 502 includes first sleeve walls 506 and the second sleeve includes second sleeve walls 508. The first sleeve 502 may freely rotate about the central axis 534 with respect to the second sleeve 504, and translate parallel to the central axis 534 (in one aspect, all other translational and rotational motion of the first sleeve 502 with respect to the second sleeve 504 are constrained). Although specific components of the palm-press dispensing mechanism 500 are referred to herein as being contained within either the first sleeve 502 or the second sleeve 504, a person of ordinary skill will understand that the components may generally be contained in either sleeve unless explicitly stated or otherwise clear from the text.

The first sleeve 502 may generally include a base 510 that includes a cap 512. The first sleeve 502 may also include a dispenser tube 514 that protrudes through the base 510. Additionally, the first sleeve may include an agitator 516.

The base 510 may include the cap 512 or any other structure that effectively seals the first sleeve 502. The base 510 may be located a first distance from the top 518 of the palm-press dispensing mechanism 500 (which may be disposed on the second sleeve 504) when the palm-press dispensing mechanism 500 is in the uncompressed state, and the base 510 may be located a second distance from the top 518 when the palm-press dispensing mechanism 500 is in the compressed state, where the first distance is greater than the second distance.

The cap 512 may effectively seal the first sleeve 502. The cap 512 may also include a dispensing hole 520 for the device. The dispensing hole 520 may be the orifice in which the dispenser tube 514 (or a portion thereof, e.g., an item seat 522) protrudes during a dispensing operation. The cap 512 may contain a rocker mechanism that can fit a desired number of items.

The dispenser tube 514 may include an item seat 522. The item seat 522 may be concealed by the base 510 of the first sleeve 504 when the palm-press dispensing mechanism 500 is in the uncompressed state. The item seat 522 may be exposed when the palm-press dispensing mechanism 500 is in the compressed state. The dispenser tube 514 may be situated within the palm-press dispensing mechanism 500 below an item hole 524 included as part of the second sleeve 504. The item seat 522 may be sized and shaped to fit one or more items. For example, the item may have a specific item size and item shape, and the dispenser tube 514 may include a size and shape configured to cooperate with the item size and item shape to dispense the item. The dispenser tube 514 may be removable and replaceable with a second dispenser tube having at least one of a different size, shape and material. Such a removal or replacement may occur, for example, on a factory line, where physically different dispenser tubes may be attached to an otherwise standard palm-press dispensing mechanism. The dispenser tube 514 may be part of, or connected to, the first sleeve 502, the second sleeve 504, or it may be a separate piece altogether. For example, the dispenser tube 514 may be connected to the first sleeve 502 via a snap retaining feature or the like.

The agitator 516 may include an asymmetrical shape, and or be located off-center from the central axis 534 of the palm-press dispensing mechanism 500. The agitator 516 may protrude from the base 510 of the first sleeve 502, where it is disposed at least partially beneath the chute 526 in the uncompressed state and disposed at least partially within the chute 526 in the compressed state. The agitator 516 may seal the agitator hole 528 of the chute 526 in the uncompressed state, where the agitator prevents items from falling through the agitator hole 528. Alternatively, the agitator hole 528 may be sized such that items may not pass through. The motion and/or the shape of the agitator 516 may assist the palm-press dispensing mechanism 500 in directing items toward the item hole 524. The agitator 516 may be connected to the cap 512 using a snap retaining feature or the like. As discussed below, the agitator 516 may be movable in relation to the second sleeve 504 and the chute 526.

The second sleeve 504 may generally include the second sleeve walls 508 and the top 518, which generally form the structure of the second sleeve 504. The second sleeve 504 may also include the chute 526.

The chute 526 may include an item hole 524 disposed at the base of the chute 526, and an agitator hole 528 to accommodate at least a portion of the agitator 516 when the palm-press dispensing mechanism 500 is in the compressed state. The chute 526 may generally be a component that is positioned to receive the items from the reservoir 530 and guide the items to a user-accessible location. As shown in FIGS. 5A and 5B, the reservoir 530 may be contained within the second sleeve 504. However, one of ordinary skill will recognize that the palm-press dispensing mechanism 500 may be attached to a separate container including a reservoir that houses the items. As shown in FIGS. 5A and 5B, the chute 526 may include a substantially funnel-shape structure having ramped surfaces 532, which may be asymmetrical ramped surfaces 532, e.g., including different slopes and with the item hole 524 off-center from a central axis 534. The asymmetrical shape may assist in preventing the items from jamming within the palm-press dispensing mechanism 500. The chute 526 may include a chute path 536 that guides the items from the reservoir 530 to the item hole 524 and into the dispenser tube 514, which receives the item in the item seat 522 and allows a user to access the item when in the compressed state. The agitator 516 may assist with guiding the items into the item hole 524 of the chute 526. The location of the item hole 524 and agitator 516, combined with one or both of the sloped ramped surfaces 532 and the asymmetric shape of the agitator 516, may assist in preventing jamming due to a concentration of items at the center of the palm-press dispensing mechanism 500 (e.g., from uniform gravitational pull). The chute 526 may be connected to the second sleeve 504 using a snap retaining feature or the like.

The operation of a palm-press dispensing mechanism will now be described.

In operation, a user may actuate the palm-press dispensing mechanism 500 by applying a pressing force normal to the cap 512 to an end of the palm-press dispensing mechanism 500 (e.g., an end of the first or second sleeve 502, 504). When a pressing force is applied, the first sleeve 502 and the second sleeve 504 may slide relative to one another along the first and second sleeve walls 506, 508 thereby creating the compressed state (where the base 510 and the top 518 are separated by a smaller distance than a distance between the base 510 and the top 518 when the device is in an uncompressed state). Also, when the first sleeve 502 and the second sleeve 504 slide relative to one another to create the compressed state, the agitator 516 may protrude through the agitator hole 528 of the chute 526. The motion of the agitator 516 combined with the shape of the agitator 516 may thereby agitate the items and direct at least one of the items through the item hole 524 and onto the item seat 522 of the dispenser tube 514. In this manner, because the item seat 522 of the dispenser tube 514 is exposed when the palm-press dispensing mechanism 500 is in the compressed state, the item disposed on the item seat 522 is also exposed and thereby dispensed.

The palm-press dispensing mechanism may include child-proofing.

Figure 6:
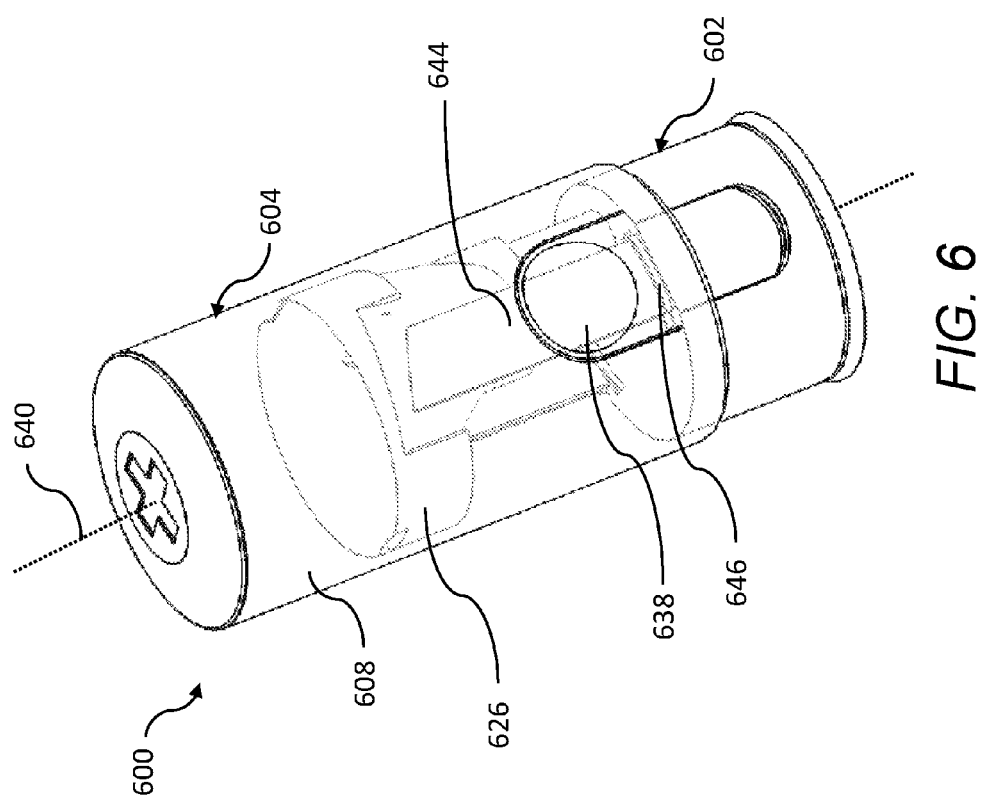
FIG. 6 is a side perspective view of a palm-press dispensing mechanism in an uncompressed state.

As best shown in FIG. 6, the childproofing in the palm-press dispensing mechanism 600 may be enabled by the inclusion of tabs 638. Specifically, tabs 638 may be disposed on the second sleeve walls 608, where they are movable toward a central axis 640 of the palm-press dispensing mechanism 600 when a tab pressing force normal to the central axis 640 is applied to the tabs 638. The palm-press dispensing mechanism 600 may further include protrusions 644 extending from the chute 626 (or other component of the palm-press dispensing mechanism 600) disposed adjacent to the tabs 638. The protrusions 644 may be movable with the tabs 638. The palm-press dispensing mechanism 600 may further include notches 646 disposed on the first sleeve 602. The notches 646 may be releasably engaged with the protrusions 644 when the palm-press dispensing mechanism 600 is in the uncompressed state, where the engagement between the protrusions 644 and the notches 646 prevents movement of the first sleeve 602 relative to the second sleeve 604. When a user applies the tab pressing force to the tabs 638, the tabs 638 may move the protrusions 644 toward the central axis 640 disengaging the protrusions 644 from the notches 646 and allowing the first sleeve 602 and the second sleeve 604 to slide relative to one another to create the compressed state (when the pressing force normal to the cap 612 is also applied to an end of the palm-press dispensing mechanism 600).

A counting mechanism will now be described.

FIGS. 7A and 7B show cross-sectional views of a counting mechanism 700, where FIG. 7A shows a first position and FIG. 7B shows a second position. In general, the counting mechanism 700 may be used with any of the devices described herein or any dispensing devices known or that will be known in the art. For example, the counting mechanism 700 may be used in conjunction with a housing including a reservoir configured to hold a plurality of items, a cap for the housing, where the cap includes a dispensing hole, and a chute coupled to the reservoir, where the chute includes a dispensing path to direct at least one of the items through the dispensing hole. In general, the counting mechanism 700 may increment each dispensing operation, which could be useful if dispensing, e.g., a dose of medication. The counting mechanism 700 may generally include a rocker mechanism 702, a biasing member 704, a pin 706, and a dial counter 708. The counting mechanism's 700 count may represent, for example: (1) the total number of items dispensed since opening, or (2) the total number of items remaining. As described below, reliable counting may be enabled in the following manner: (1) the rocker mechanism 702 may not engage if an item is not inside it, in other words, if the user actuates the dispenser but no item comes out, the counting mechanism 700 may not increment; and (2) the rocker mechanism 702 may not engage until the item has left it, in other words, if the user does not extract the dispensed item (assuming the item has not left the rocker mechanism 702), the counting mechanism 700 may not increment.

The rocker mechanism 702 may be included along a dispensing path of a dispensing device in communication with the dispensing hole (e.g., located along the dispensing path before the dispensing hole or after the dispensing hole). For example, the rocker mechanism 702 may be located adjacent to an exterior of the dispensing hole. The rocker mechanism 702 may be pivotable about a pivot point 710, where the pivoting of the rocker mechanism 702 may be relative to the chute, dispensing hole, or other component of a dispensing device. The rocker mechanism 702 may include an item seat 712 for temporarily holding an item 714 being dispensed.

The biasing member 704 may be mechanically coupled to the rocker mechanism 702. The biasing member 704 may include a biasing force that holds the rocker mechanism 702 in the first position as shown in FIG. 7A. The rocker mechanism 702 may be pivotable into a second position as shown in FIG. 7B when a force is applied to the item seat 712, which causes compression of the biasing member 704. The force applied to the item seat 712 may include the weight of the item 714 on the item seat 712. The biasing member 704 may include a leaf spring or the like.

The pin 706 may be attached to the rocker mechanism 702. The pin 706 may be movable with the rocker mechanism 702. The pin 706 may include surfaces that come to a point, a pointed structure, an extension, a protrusion, or the like.

The dial counter 708 may be disposed within the housing of the dispensing device and/or within the counting mechanism 700. The dial counter 708 may be rotatable, e.g., relative to the housing or other component of the dispensing device. The dial counter 708 may be configured to be engaged by the pin 706 when the pin 706 completes a pivoting motion. The pin 706 may be said to complete a pivoting motion when the item 714 is dispensed, or when the counting mechanism 700 moves from the first position to the second position and back to the first position. The dial counter 708 may be a rotary counter or the like. For example, the dial counter 708 may be a rotating horizontal or vertical dial. Alternatively, the dial counter 708 may be a digital counter, where interaction with the pin 706 may be a physical interaction or otherwise (e.g., electrical, magnetic, etc.). The counting mechanism 700 may include a viewing port or the like configured to provide a view of a current count of the dial counter 708.

Operation of a counting mechanism will now be described.

The item 714 for dispensing may be directed onto the item seat 712 of the rocker mechanism 702 when the counting mechanism 700 is in the first position. The weight of the item 714 may concurrently compress the biasing member 704 and pivot the rocker mechanism 702 into the second position. The second position may include a position of the item seat 712 where the item 714 is released from the item seat 712, e.g., due to gravity. Releasing the item 714 for dispensing from the item seat 712 may cause the biasing member 704 to pivot the rocker mechanism 702 back into the first position. The pin 706 may engage the dial counter 708 through this range of motion, e.g., upon the movement from the first position to the second position or upon the return from the second position to the first position, or incrementally through all motions. The engagement of the pin 706 with the dial counter 708 may cause the dial counter 708 to rotate, where the rotation thereby counts a number of items 714 dispensed by the counting mechanism 700 or device.

Additional features of the devices, systems, and methods described herein will now be discussed.

In one aspect, the device may include at least one of a door and/or at least one window. The door may be in cooperation with the reservoir and be configured to allow access to the plurality of items in the reservoir. The window may include a translucent surface in cooperation with the reservoir and be configured to allow viewing of the plurality of items in the reservoir. For example, the reservoir may have a door on one of its faces, which could allow for users to add or remove any number of items, and which may have a visual indication upon it that warns users not to insert incompatible media. In one implementation, this door may be a simple face that swings open on a hinge once a latch is released. In another aspect, this door may be a face cap-like piece that snaps into place and may or may not be removable. In one aspect, the reservoir housing the items may be transparent or translucent.

The device as described may, in acting as a cartridge, interact with one or more configuration devices, such as a holder, a base and/or a clip. A holder may store cartridges or other attached devices. A base may manage, dispense and/or store consumables from attached cartridges or other devices. For example, the base may include a dispensing mechanism as described herein. A clip may be a lightweight, mobile attachment to one or more cartridges.

The cartridge may have an aesthetic design which may have either a polygon or a round base. The cartridge may have multiple reservoirs, where reservoirs may accept the same or different media/media properties. Generally, while a single reservoir is depicted, it will be understood that a cartridge may have any number of reservoirs, and may be configured for independent dispensing from each reservoir, or dispensing in combination from multiple reservoirs. The reservoirs may be configured for either or both of similar or different media types (i.e., items). By way of example, one of the cartridges may include at least two types of consumable units in at least two independently dispensing reservoirs. More generally, one of the cartridges or any number of the cartridges may include three or more types of consumables in three or more independently dispensing reservoirs. The independently dispensing reservoirs may be independently controllable by the dispensing mechanism in order to permit customized consumable units based on mixtures of the two or more types of consumables. The two independently dispensing reservoirs may also or instead be commonly controlled by the dispensing mechanism to provide a mixed consumable having a predetermined composition in response to a single dispense instruction from the dispensing mechanism. The cartridge may also include a mixing system such as a stirring system, blending system, agitation system, pill press, and the like to combine the two types of consumable units into a single, composite consumable unit, which may be a pill, a capsule, a suspension, and a solution. In this manner, a cartridge may serve as a personal compounding system for home-made medications, supplements, and so forth.

In one aspect, multiple dispensing mechanisms could function as modules and attach to each other, in a manner that for instance connects their chutes together into one or more integrated chutes.

The dispensing mechanisms and counting mechanism may work universally with different item sizes (e.g., different pill shapes and sizes), in at least one of several ways such as the two following: (1) for each grouping of item size/shape, there may be slightly different mechanism dimensions (achieved by slight variations on the mold tooling and manufacturing line), though the exterior form does not change; (2) there may be a universal mechanism with a small collar within that is adjusted, e.g., on the packaging line for different groupings of item size/shape.

In one aspect, the device may include a memory, for example, a memory configured to store data regarding the item. The memory may be configured to store the numeric count of the number of items in the cartridge or dispensing mechanism. The cartridge or dispensing mechanism may include circuitry configured to detect the numeric count of the number of consumable units. The system may include an order fulfillment system. The device may be configured to dispense items from one or more cartridges according to a predetermined schedule, and the order fulfillment system may compare the numeric count of the plurality of items to the predetermined schedule to determine when a replacement cartridge should be ordered for the user. The order fulfillment system may include computer code executing on the processor of the base. The order fulfillment system may also or instead include computer code executing on a remote server coupled in a communicating relationship through a data network to the device. The order fulfillment system may be configured to order the replacement cartridge. The order fulfillment system may be configured to notify the user to order the replacement cartridge.

The system may include cartridge data for one of the cartridges stored in a cartridge memory, along with a remote data store that redundantly stores the cartridge data. The cartridge memory may reside in the base, or in one of the cartridges. A reconciliation service may be provided to reconcile data between the remote data store and the cartridge memory.

The system may include a network interface for coupling one of the cartridges to the data network, with the network interface configured to transmit data between the cartridge and a remote resource according to a priority. In this manner, data may be prioritized, such as in limited connectivity contexts, to ensure that the most important or highest priority data is exchanged first. The priority may be based on a degree of redundancy so the least redundant data is exchanged first. The prioritization may occur at any point in the corresponding data connection, and may for example be implemented in one or more of the cartridge, the base, and the remote resource. In one aspect, the network interface may include a wireless communication interface in the one of the cartridges, which may couple in a communicating relationship to, e.g., the base station with a short range wireless protocol or a wide area data network using a cellular or other wireless data network infrastructure.

It should further be appreciated that the methods above are provided by way of example. Absent an explicit indication to the contrary, the disclosed steps may be modified, supplemented, omitted, and/or re-ordered without departing from the scope of this disclosure.

The method steps of the invention(s) described herein are intended to include any suitable method of causing such method steps to be performed, consistent with the patentability of the following claims, unless a different meaning is expressly provided or otherwise clear from the context. So for example performing the step of X includes any suitable method for causing another party such as a remote user, a remote processing resource (e.g., a server or cloud computer) or a machine to perform the step of X. Similarly, performing steps X, Y and Z may include any method of directing or controlling any combination of such other individuals or resources to perform steps X, Y and Z to obtain the benefit of such steps. Thus method steps of the implementations described herein are intended to include any suitable method of causing one or more other parties or entities to perform the steps, consistent with the patentability of the following claims, unless a different meaning is expressly provided or otherwise clear from the context. Such parties or entities need not be under the direction or control of any other party or entity, and need not be located within a particular jurisdiction.

It will be appreciated that the methods and systems described above are set forth by way of example and not of limitation. Numerous variations, additions, omissions, and other modifications will be apparent to one of ordinary skill in the art. In addition, the order or presentation of method steps in the description and drawings above is not intended to require this order of performing the recited steps unless a particular order is expressly required or otherwise clear from the context. Thus, while particular embodiments have been shown and described, it will be apparent to those skilled in the art that various changes and modifications in form and details may be made therein without departing from the spirit and scope of this disclosure and are intended to form a part of the invention as defined by the following claims, which are to be interpreted in the broadest sense allowable by law.

What is claimed is:

1. A device comprising:
   a reservoir configured to hold a plurality of items;
   a chute coupled to the reservoir, the chute including a chute path to direct at least one of the items into a position for dispensing;
   a housing about the reservoir and the chute;
   a cap for the housing, the cap including a dispensing hole, and the cap movably coupled relative to the chute to permit the dispensing hole to move into and out of alignment with the position for dispensing;
   an agitator positionable within the reservoir;
   an actuator mechanically coupled to the agitator and the cap, the actuator configured to concurrently move the agitator within the reservoir to agitate the items and move the cap relative to the chute to align the dispensing hole with the position for dispensing;
   a first sleeve of the housing, the first sleeve including first sleeve walls and a base comprising the cap, the first sleeve further including the agitator;
   a second sleeve of the housing including second sleeve walls and a top, the second sleeve slidably engaged with the first sleeve such that, when a pressing force normal to the cap is applied to an end of the device, the first sleeve and the second sleeve slide relative to one another along the first and second sleeve walls thereby creating a compressed state for the device where the base and the top are separated by a smaller distance than a distance between the base and the top when the device is in an uncompressed state; and a dispenser tube protruding through the base of the first sleeve and including an item seat, wherein the item seat is concealed by the base of the first sleeve when the device is in the uncompressed state, and wherein the item seat is exposed when the device is in the compressed state, wherein the chute is disposed within the second sleeve, and wherein the chute includes an item hole and an agitator hole, wherein the dispenser tube is situated below the item hole, and wherein, when the first sleeve and the second sleeve slide relative to one another to create the compressed state for the device, the agitator protrudes through the agitator hole of the chute thereby agitating the items and directing one of the items through the item hole and onto the item seat of the dispenser tube such that one of the items is exposed when the device is in the compressed state.

2. The device of claim 1 wherein the chute includes surfaces asymmetrically arranged about an axis of the reservoir, the surfaces forming the chute path.

3. The device of claim 1 wherein the agitator includes an asymmetrical shape.

4. The device of claim 1 further comprising at least one container including the plurality of items, the at least one container engaged with the housing using at least one of: a snap-fit connection, a screw connection, a friction-fit connection, a pronged connection, and an electromagnet connection.

5. The device of claim 1 further comprising an attachment coupled to the housing by an attachment mechanism, wherein one the items is dispensed through the dispensing hole and into the attachment.

6. The device of claim 1 further comprising a memory configured to store data regarding the items.

7. The device of claim 1 further comprising at least one of a door and a window, the door in cooperation with the reservoir and configured to allow access to the plurality of items in the reservoir, the window including a translucent surface in cooperation with the reservoir and configured to allow viewing of the plurality of items in the reservoir.

8. The device of claim 1 wherein each of the items has a specific item size and item shape, and wherein the dispenser tube includes a size and shape configured to cooperate with the item size and item shape and to dispense one of the items.

9. The device of claim 8 wherein the dispenser tube is removable and replaceable with a second dispenser tube having at least one of a different size and shape.

10. The device of claim 1 further comprising:
a first surface at a base of the reservoir, the first surface including a first hole; and
a second surface disposed below the first surface and rotatably coupled to the first surface, the second surface including a second hole configured for alignment with the first hole when the first surface and the second surface are placed in a predetermined rotational alignment relative to one another, wherein alignment of the first hole with the second hole forms the dispensing hole for the device.

11. The device of claim 1 wherein the dispensing hole is formed in the dispenser tube, the dispenser tube removable from and replaceable to the device to facilitate replacement of the dispenser tube with a second dispenser tube shaped having a second dispensing hole configured to dispense different items having a different shape or size from the plurality of items.

12. The device of claim 1 further comprising an adjustable component in-line with the dispensing hole and configured to adjust a size of the dispensing hole to dispense different items having a different size or shape from the plurality of items.

* * * * *